United States Patent
Loginova et al.

(10) Patent No.: US 6,524,565 B1
(45) Date of Patent: Feb. 25, 2003

(54) WATER RESISTANT, WEAR RESISTANT, AND DECORATIVE COSMETIC FOR HAIR

(75) Inventors: Yelena Loginova, Bronx, NY (US); Domnica Cernasov, Ringwood, NJ (US); Ralph Macchio, Sparta, NJ (US)

(73) Assignee: Coty B. V. (NL)

( * ) Notice: Subject to any disclaimer, the term of this patent is extended or adjusted under 35 U.S.C. 154(b) by 0 days.

(21) Appl. No.: 09/965,578

(22) Filed: Sep. 27, 2001

(51) Int. Cl.[7] .......................... A61K 7/025; A61K 7/06
(52) U.S. Cl. .................. 424/70.7; 424/64; 424/70.1
(58) Field of Search .................. 424/64, 70.6, 70.7, 424/401

(56) References Cited

U.S. PATENT DOCUMENTS 5,389,363 A * 2/1995 Snyder et al. ............. 424/70.7

* cited by examiner

Primary Examiner—Thurman K. Page
Assistant Examiner—S. Howard
(74) Attorney, Agent, or Firm—Schwegman, Lundberg, Woessner & Kluth, P.A.

(57) ABSTRACT

The invention refers to a cosmetic product for hairs and decorative cosmetic with particular water resistance and wear (transfer) resistance. The product comprises stabile mixture of a water-emulsifiable, film-forming agent; a rheology modifier; a pigment; a volatile organic solvent; an oil soluble polymeric film-former; a silicon resin; and a filler.

25 Claims, No Drawings

WATER RESISTANT, WEAR RESISTANT, AND DECORATIVE COSMETIC FOR HAIR

RELATED APPLICATIONS

This application claims priority to German Patent Application No. 101 368 83.6, filed Jul. 24, 2001.

BACKGROUND

The present invention relates to a cosmetic product for hair, such as eyelash hair and eyebrow hair and decorative cosmetic with particular water resistance and wear (transfer) resistance.

From U.S. Pat. No. 5,925,337 a waterproof mascara composition is known which contains 2–40% by weight of a wax, 5–15% by weight of a thickening agent, 35–50% by weight of a volatile organic solvent and 1–35% by weight of a water-soluble film-forming agent, wherein the last-named agent may e.g. also be an acrylate polymer. The composition does not contain any emulsifier.

SUMMARY OF THE INVENTION

One embodiment of the present invention includes a water-resistant cosmetic gel. The gel comprises a stable mixture, comprising a water-emulsifiable, film-forming agent selected from one or more of an acrylate copolymer or acrylic or methacrylic acid or an ester thereof, a water-immiscible aliphatic hydrocarbon solvent, a non-ionic emulsifier and water; a cosmetic wax; a rheology modifier; a pigment phase; a volatile organic solvent; an oil soluble polymeric film-former; a silicon resin and a filler. The pigment comprises one or more of mineral pigments, organic pigments, pearl pigments, surface-coated pigments and mixtures thereof.

Another embodiment of the present invention includes a cosmetic gel. The cosmetic gel comprises a stable mixture comprising ethyl acrylate and methyl methacrylate in a concentration of about 24.5% by weight of the gel and isododecane in a concentration of about 50% by weight of the gel.

Another embodiment of the present invention includes an eyebrow color cosmetic. The eyebrow color cosmetic comprises a mixture comprising Carnauba wax, beeswax, castor wax, microcrystalline wax and PVP/Eicosane copolymer. The eyebrow color cosmetic also includes a pigment in a concentration of about 6% of the cosmetic. Other ingredients include trimethylsiloxysilicate and decamethylcyclopentasiloxane and the gel of the present invention.

One other embodiment of the present invention includes a method for imparting elasticity and softness to a cosmetic. The method comprises providing a film-forming agent comprising an acrylate copolymer or acrylate derivative and a non-ionic emulsifier to form a mixture. The method also includes heating the mixture to a temperature f 45 to 50 degrees Centigrade to form an emulsion. The method further includes mixing the emulsion with a volatile aliphatic hydrocarbon solvent or a volatile silicone derivate and homogenizing to form a two-phase liquid system. The method further includes cooling the two-phase liquid system with rapid mixing to form a homogeneous gel and mixing the gel with a cosmetic formulation to soften and increase elasticity of the cosmetic formulation.

DETAILED DESCRIPTION

The present invention provides a new cosmetic product for hair and a decorative cosmetic which, due to its special structure, is suitable for forming a soft and elastic product with waterproof characteristics and improved prolonged wear.

According to the invention, the cosmetic product for hair and decorative cosmetic which comprises
- 1–45% by weight of a stable mixture of a water-emulsifiable, film-forming agent on the basis of an acrylate copolymer or of acrylic or methacrylic acid or an ester thereof, a water-immiscible aliphatic hydrocarbon solvent, a non-ionic emulsifier and water;
- 1–45% by weight of a cosmetic wax;
- 0.1–10% by weight of a rheology modifier;
- 0.1–30% by weight of a pigment phase, comprising mineral pigments, organic pigments, pearl pigments, surface-coated pigments and mixtures thereof;
- 51–90% by weight of a volatile organic solvent;
- 1–15% by weight of an oil soluble polymeric film-former;
- 0.01–30% by weight of a silicon resin;
- 0.01–20% by weight of a filler;

and wherein all percents are related to the total weight of the cosmetic composition.

The stable mixture with an acrylate copolymer, a hydrocarbon solvent, an emulsifier and water preferably contains 0.01–30% by weight of a film-forming agent on the basis of an acrylate copolymer or acrylic or methacrylic acid or an ester of acrylic or methacrylic acid, which agent is emulsifiable with water; 0.01–35% by weight of an aliphatic hydrocarbon solvent or a volatile silicone derivate, both of which are not miscible with water and are emulsifiable with water-based ingredients and/or with ingredients on the basis of organic solvents in the presence of an emulsifier; 0.01–2% by weight of a non-ionic emulsifier; and 0.1–30% by weight of water; and wherein the composition has the structure of a gel. All percents are related to the total weight of the cosmetic product.

Advantageously, alkoxylated alcohols, ethoxylated alcohols, polyglycerine esters and mixtures thereof can be used as emulsifier. The said substances are non-ionic emulsifiers which contain e.g. a polyol group, a polyalkylglycol ether group or a combination thereof, such as e.g. addition products of 2–30 mole ethylene oxide to linear fatty alcohols having 8–22 carbon atoms and to fatty acids having 12–22 carbon atoms, as hydrophillic group. The said substances further include polyglycerine esters, such as e.g. polyglycerine ricinoleate or polyglycerine poly-12 hydroxystearate, and mixtures of these different substance classes.

A preferred emulsifier is, for example, Laureth-20, Laureth-23, Oleth-20, Steareth-20, Steareth-50, Ceteareth-20, Ceteareth-30.

An ethyl acrylate/methyl methacrylate copolymer can be used as acrylate copolymer, for example.

It is particularly preferred that the film-forming agent be an ethyl acrylate/methyl methacrylate copolymer in which the ratio of ethyl acrylate units to methyl methacrylate units in the polymer is in the range of 7.5–8.5:1.8–2.3.

Acrylic acid, methacrylic acid or their esters also can be used (here called "acrylate derivates").

A preferred range for the acrylate copolymer in the gel is between 0.5 and 46% by weight, particularly 0.25 to 23% by weight related to the total weight of the cosmetic product.

Isoparaffins e.g. isododecane, pentane, hexane, decane or special petroleum distillates etc. are preferably used as aliphatic hydrocarbon solvent which is not miscible with water are preferred in the stable mixture with gel structure. Isododecane is special preferred.

A preferred range for the aliphatic hydrocarbon solvent or the volatile silicone derivate in the stable mixture with the gel structure is between 55 and 90% by weight, related to the total weight of the cosmetic product.

Advantageously, a compound such as cyclopentasiloxane or trimethylsiloxysilicate or a mixture thereof can be used as volatile silicone derivate. Dimethicone or trimethylsiloxysilicate are preferred silicone derivatives.

A preferred silicone derivate is e.g. deca-, methyl-, cyclo-, penta-, siloxy-, siloxane (Silicone SS4230).

The preferred water content is in the range of 1.0 to 40% by weight, particularly 1.0 to 20% by weight.

A preferred wax is a natural plant wax, animal wax, natural and synthetic mineral wax and synthetic wax. The waxes may be selected among carnauba wax, candelilla wax, ozokerite, beeswax, montan wax, wool wax, ceresine, micro-waxes, paraffin waxes, petrolatum, silicone, polyethyleneglycol(ester) waxes.

Pigments, pigment mixtures or powders with a pigment-like effect, also including those with a pearl-gloss effect, may include, for example, iron oxides, aluminum silicates such as ochre, titanium (di)oxide, mica, kaolin, manganese containing clays such as umber and red bole, calcium carbonate, French chalk, mica-titanium oxide, mica-titanium oxide-iron oxide, bismuth oxychioride, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye and other surface-treated particles.

A preferred volatile organic solvent is a hydrocarbon solvent as described above or a volatile silicone derivate.

A preferred soluble polymeric film-forming agent is selected from e.g. copolymers of vinylpyrrolidone and long-chain -olefines such as PVP/Eicosane Copolymer.

Fillers are for example talc, starch (treated or untreated), kaolin and polyamid; also certain auxiliary substances can be used such as water, preservatives, vitamins, colorings, radical scavengers, softeners, moisture-retaining substances, fragrances, polyols, pH value regulators, amino acids, proteins, polar and nonpolar oils, sequestering agents, adhesives.

The stable mixture with acrylate copolymer, hydrocarbon solvent, emulsifier and water is a gel which is particularly characterized in that a combination of solvent and film-forming agent is obtained which is stable in the cosmetic formulation. Such a stable combination having the characteristics of a gel was surprising for those skilled in the art, and it permits the manufacture of cosmetic products, such as the products of the invention, which are particularly elastic and soft. For example, in the case of an ethyl acrylate/methyl methacrylate copolymer, the elasticity can be increased 4- to 5-fold compared to the elasticity of the film-forming agent used.

The elasticity was determined using the strip test method, which is carried out as follows:

The measurement of length of an elastic film made from a polymer has been carried out. Two separate films A and B of about 150 ?m (6.0 mil) thick have been poured on the non-sticky surface with a Bird applicator. Film A consists of an aqueous acrylate copolymer (Acrylates Copolymer:Water about 50:50, emulsifier), and film B consists of 50% components of film A and 50% isododecane. In 24 hours, at 25° C., the specimens were prepared by cutting the strips of about 50×25 mm. One end of the strip was attached to a ruler. The specimen was tested by stretching the strip without breaking in the direction of the end of the ruler. The result for film A was 101 mm, for film B 406 mm.

The softness of the composition after applying it to the skin or to an even surface is also considerably higher than that of the original film-forming agent. This improves the feeling, which plays a central role in the selection of a product by the user.

The manufacture of the stable mixture with an acrylate copolymer, hydrocarbon solvent, emulsifier and water consists in that a mixture of a film-forming agent on the basis of an acrylate copolymer or acrylate derivate, water and a non-ionic emulsifier is heated up to a temperature in the range of 45–50° C.; at this temperature the obtained emulsion is mixed with a volatile aliphatic hydrocarbon solvent or a volatile silicone derivate, wherein the solvent or the silicone derivate are not miscible with water, but are emulsifiable with water-based ingredients and/or with ingredients on the basis of organic solvents in the presence of an emulsifier, and wherein a two-phase liquid system is obtained after homogenization at 1500–3000 rpm during 15–60 minutes until the organic phase which is not miscible with water is completely distributed in the aqueous phase in the form of micro-droplets; and c) the mixture is cooled down to 25–30° C. at a rate of 300 to 600 rpm until a homogeneous gel is obtained.

After that the processing takes place with the other cosmetic auxiliary cosmetic substances and/or effective cosmetic substances in usual manner at temperatures of about 35 to 40° C.

This method is characterized by a strictly defined sequence of steps and an unusual temperature regime. It is only in this way that a stable formulation having the above-mentioned advantages can successfully be obtained.

The cosmetic product of the invention can be used for hair especially for eyelashes (as mascara) and eyebrow color. More specifically, it can be used as a touch-up temporary hair colorant that fully covers the gray spots and provides a prolonged wear. The typical disadvantage of the eyelash cosmetic including waterproof mascara of the market is the unsatisfactory durability effect such as durability of water resistance and skin oil resistance. The cosmetic of the invention provides an improvement in water resistance for the all day wear over a longer period and satisfactory skin oil resistance.

In the use direction of decorative cosmetic, that means for lip color, cream blush, foundations, make-up, cream eye shadow, concealer, mascara, eye brown color etc. also a significant improvement will be reached with respect to known products of the market, both in wear resistance and water resistance for a longer period (up to 24 hours) and under different environment conditions. Also an unpleasant tacky or smearing feeling will not be present such as known for usual products of the market. The cosmetic of the invention does stay on under the shower or swimming or rain and shows a non-drying effect to the skin.

The invention will hereinafter be explained more precisely by means of examples which, however, do not constitute any limitation of the invention. All quantities are given in percent by weight.

EXAMPLE 1

Basic Gel

| | |
|---|---|
| Ethyl acrylate/methyl methacrylate | 24.5 |
| Water | 25.0 |
| Laureth-20 | 0.3 |
| Isododecane | 50.0 |

The copolymer is mixed with water and the emulsifier Laureth-20, and the mixture is heated up to 45 C. Isododecane is added, and the temperature is increased to 50 C. while stirring. After than homogenization takes place at 2200 rpm for a time of 18 minutes in a laboratory vessel of 1000 ml volume. Subsequently, the mixture is cooled down to 27 C. and stirred at a rate of 400 rpm for approx. 5 minutes.

EXAMPLE 2
Eyebrow Color

| | |
|---|---|
| Carnauba Wax | 4.9 |
| Bees Wax | 3.3 |
| Castor Wax | 1.4 |
| Microcrystalline Wax | 5.0 |
| PVP/Eicosane Copolymer | 4.0 |
| Pigments | 6.0 |
| Isododecane | 38.5 |
| Disteardimoninium Hectorite | 4.0 |
| Isododecane | 13.0 |
| Propylene Carbonate | 1.6 |
| Trimethylsiloxysilicate and Decamethylcyclopentasiloxane | 2.0 |
| Basic gel from Example 1 | 16 |
| Preservatives (Parabens) | 0.3 |

The wax phase was melt at 85° C. After that pigments are added to the wax phase and homogenized. Isododecane was added with maintaining the temperature at ca. 60° C. Clay has been pre-mix with Isododecane and added to the batch. The remaining ingredients were added at ca. 40° C. and the mixture was homogenized.

EXAMPLE 3
Mascara

| | |
|---|---|
| Carnauba Wax | 5.1 |
| Beeswax | 4.0 |
| Castor Wax | 1.9 |
| Paraffin | 6.0 |
| PVP/Eicosane Copolymer | 5.5 |
| Propylparaben | 0.2 |
| Pigments | 8.0 |
| Petroleum Distillates | 45.0 |
| Disteardimoninium Hectorite | 3.0 |
| Petroleum Distillates | 12.0 |
| Propylene Carbonate | 1.2 |
| Basic gel from Example 1 | 6.0 |
| Cylopentasiloxane (and) Trimethylsiloxysilicate | 2.1 |

The method of working was like Example 2.

Comparative Example 4

The mascara of Example 3 (Product A) was tested for its waterproof properties for consumer evolution in comparison with waterproof products of the market with known brands (Product B ". . . volume express WP" and product C". . . voluminous WP"). The rating by 23 panelist took place on a scaling from 0 to 5; 0=worst rating, 5=best rating.

| | Product A | Product B | Product C |
|---|---|---|---|
| Waterproof | 4.4 | 3.7 | 3.4 |
| Avoidance of flaking | 3.7 | 3.2 | 2.9 |
| Avoidance of clumping | 3.6 | 2.8 | 2.6 |

| | Product A | Product B | Product C |
|---|---|---|---|
| Overall comfort of the product during wear | 4.4 | 3.6 | 3.1 |

A significant improvement of product A (invention) was shown with an average of 15 to 30%.

EXAMPLE 5
Semi-matte Long Wearing Transfer-proof Lip Color A

| | |
|---|---|
| Carnauba Wax | 4.9 |
| Bees Wax | 3.3 |
| Castor Wax | 1.4 |
| Microcrystalline Wax | 5.0 |
| PVP/Eicosane Copolymer | 4.0 |
| Pigments | 5.0 |
| Isododecane | 40.5 |
| Stearalkoninium Hectorite | 4.0 |
| Isododecane | 13.0 |
| Propylene Carbonate | 1.6 |
| PPG-51/SMDI Copolymer | 2.0 |
| Basic gel from Example 1 | 16 |
| Preservatives (Parabens) | 0.3 |

The method of working was like Example 2.

EXAMPLE 6
Long-Wearing Blush B

| | |
|---|---|
| Carnauba Wax | 4.9 |
| Bees Wax | 3.3 |
| Castor Wax | 1.4 |
| Microcrystalline Wax | 5.0 |
| PVP/Eicosane Copolymer | 3.0 |
| Pigments | 5.0 |
| Isododecane | 39.5 |
| Disteardimoninium Hectorite | 4.0 |
| Isododecane | 13.0 |
| Propylene Carbonate | 1.6 |
| Trimethylsiloxysilicate and Decamethylcyclopentasiloxane | 2.0 |
| Rice starch | 1.0 |
| Basic gel of Example 1 | 16 |
| Preservatives (Parabens) | 0.3 |

The method of working was like Example 2.

Comparative Example 7
Kiss Test

The lip color of example 5 were applied to the lips of 12 panelists an allowed to set for 3 min. The panelists were asked to kiss their hands and rate the samples in a scaling from 1 to 5 (1=not acceptable, 5=excellent) the transfer/wear. 10 of 12 panelists rated the lip color A by 5 in terms of "did not leave a trace of color", 2 panelists rated it by 4 "did leave a trace of color".

Comparative Example 8

Blush Test

The blush test was carried out similar as the kiss test by 12 panelists after applying the blush of Example 6 on a cheek. All panelists rated the transfer resistance with score 5=excellent.

What is claimed is:

1. A water-resistant cosmetic gel, comprising:
   a stable mixture, comprising a water-emulsifiable, film-forming agent, selected from one or more of an acrylate copolymer or acrylic or methacrylic acid or an ester thereof, a water-immiscible aliphatic hydrocarbon solvent, a non-ionic emulsifier and water;
   a cosmetic wax;
   a rheology modifier;
   a pigment phase, comprising mineral pigments, organic pigments, pearl pigments, surface-coated pigments and mixtures thereof;
   a volatile organic solvent;
   an oil soluble polymeric film-former;
   a silicon resin; and
   a filler.

2. The cosmetic gel of claim 1, wherein the stable mixture with an acrylate comprises 1–45% by weight of the film-forming agent on the basis of an acrylate copolymer or acrylic or methacrylic acid or an ester thereof which agent is emulsifiable with water.

3. The cosmetic gel of claim 1, wherein the stable mixture comprises 0.01–35% by weight of an aliphatic hydrocarbon solvent or a volatile silicone derivate, both of which are not miscible with water and are emulsifiable with water-based ingredients and/or with ingredients on the basis of organic solvents in the presence of an emulsifier.

4. The cosmetic gel of claim 1, wherein the stable-mixture comprises 0.1–2% by weight of a non-ionic emulsifier.

5. The cosmetic gel of claim 1, wherein the stable mixture comprises 1–30% by weight of water.

6. The cosmetic gel of claim 1, wherein the emulsifier is chosen from the group consisting of alkoxylated alcohols, ethoxylated alcohols, polyglyceryl esters and mixtures thereof.

7. The cosmetic gel according to claim 1, wherein the film-forming agent is an acrylate copolymer.

8. The cosmetic gel of claim 1, wherein the acrylate copolymer comprises an ethyl acrylate/methyl methacrylate copolymer.

9. The cosmetic gel of claim 1, wherein the film-forming agent is an ethyl acrylate/methyl methacrylate copolymer in which the ratio of ethyl acrylate units to methyl methacrylate units in the polymer is in the range of 7.5–8.5:1.8–2.3.

10. The cosmetic gel of claim 1, the gel having an elasticity that is four to five times greater than elasticity of the film-forming agent used to make the gel.

11. The cosmetic gel of claim 1, the gel having a softness that is greater than that of the film-forming agent used to make the gel.

12. A lip coloring agent comprising the cosmetic gel of claim 1.

13. A cream blush comprising the cosmetic gel of claim 1.

14. A cosmetic foundation comprising the cosmetic gel of claim 1.

15. A make-up comprising the cosmetic gel of claim 1.

16. A cream eyeshadow comprising the cosmetic gel of claim 1.

17. A concealer comprising the cosmetic gel of claim 1.

18. A mascara comprising the cosmetic gel of claim 1.

19. An eye cosmetic comprising the cosmetic gel of claim 1.

20. A temporary eyelash hair coloring comprising the cosmetic gel of claim 1.

21. A temporary eyebrow hair coloring comprising the cosmetic gel of claim 1.

22. A cosmetic gel comprising a stable mixture comprising ethyl acrylate and methyl methacrylate in a concentration of about 24.5% by weight of the gel and isododecane in a concentration of about 50% by weight of the gel.

23. An eyebrow color cosmetic, comprising:
   a mixture comprising Carnauba wax, beeswax, castor wax microcrystalline wax and PVP/Eicosane copolymer;
   pigment in a concentration of about 6% of the cosmetic;
   Isododecane, disteardimonium hectorite, and propylene carbonate;
   trimethylsiloxysilicate and decamethylcyclopentasiloxane; and gel of claim 1.

24. A mascara, comprising:
   Carnauba wax, beeswax, castor oil, paraffin, PVP/Eicosane copolymer and propylparaben;
   pigment in a concentration of 8% of the mascara;
   petroleum distillates in a concentration of 45%; and the gel of claim 1.

25. A method for imparting elasticity and softness to a cosmetic, comprising:
   providing a film-forming agent comprising an acrylate copolymer or acrylate derivative and a non-ionic emulsifier to form a mixture;
   heating the mixture to a temperature of 45 to 50 degrees Centigrade to form an emulsion;
   mixing the emulsion with a volatile aliphatic hydrocarbon solvent or a volatile silicone derivate and homogenizing to form a two-phase liquid system;
   cooling the two-phase liquid system with rapid mixing to form a homogeneous gel; and
   mixing the gel with a cosmetic formulation to soften and increase elasticity of the cosmetic formulation.

* * * * *

UNITED STATES PATENT AND TRADEMARK OFFICE
CERTIFICATE OF CORRECTION

PATENT NO. : 6,524,565 B1
DATED : February 25, 2003
INVENTOR(S) : Ralph Macchio, Yelena Loginova and Domnica Cernasov It is certified that error appears in the above-identified patent and that said Letters Patent is hereby corrected as shown below:

<u>Column 7,</u>
Line 30, delete "stable-mixture" and insert -- stable mixture -- therefor.

Signed and Sealed this

First Day of July, 2003

JAMES E. ROGAN
*Director of the United States Patent and Trademark Office*